US010421802B2

(12) United States Patent
Dimitrov et al.

(10) Patent No.: US 10,421,802 B2
(45) Date of Patent: Sep. 24, 2019

(54) HUMAN MONOCLONAL ANTIBODIES AGAINST THE MIDDLE EAST RESPIRATORY SYNDROME CORONAVIRUS (MERS-COV) AND ENGINEERED BISPECIFIC FUSIONS WITH INHIBITORY PEPTIDES

(71) Applicants: The United States of America, as represented by the Secretary, Department of Health and Human Services, Bethesda, MD (US); Versitech Limited, Hong Kong (HK)

(72) Inventors: Dimiter S. Dimitrov, Frederick, MD (US); Tianlei Ying, Frederick, MD (US); Tina W. Ju, Ashburn, VA (US); Kwok Yung Yuen, Hong Kong (CN)

(73) Assignees: The United States of America, as represented by the Secretary, Department of Health and Human Services, Bethesda, MD (US); Veritech Limited, Hong Kong (HK)

( * ) Notice: Subject to any disclaimer, the term of this patent is extended or adjusted under 35 U.S.C. 154(b) by 402 days.

(21) Appl. No.: 15/030,165

(22) PCT Filed: Oct. 16, 2014

(86) PCT No.: PCT/US2014/060863
§ 371 (c)(1),
(2) Date: Apr. 18, 2016

(87) PCT Pub. No.: WO2015/057942
PCT Pub. Date: Apr. 23, 2015

(65) Prior Publication Data
US 2016/0264647 A1 Sep. 15, 2016

Related U.S. Application Data

(60) Provisional application No. 61/892,750, filed on Oct. 18, 2013.

(51) Int. Cl.
*C07K 16/10* (2006.01)
*A61K 39/42* (2006.01)
*A61K 45/06* (2006.01)
*C07K 14/005* (2006.01)
*C12N 7/00* (2006.01)
*G01N 33/569* (2006.01)

(52) U.S. Cl.
CPC ............ *C07K 16/10* (2013.01); *A61K 39/42* (2013.01); *A61K 45/06* (2013.01); *C07K 14/005* (2013.01); *C12N 7/00* (2013.01); *G01N 33/56983* (2013.01); *C07K 2317/21* (2013.01); *C07K 2317/31* (2013.01); *C07K 2317/526* (2013.01); *C07K 2317/55* (2013.01); *C07K 2317/622* (2013.01); *C07K 2317/76* (2013.01); *C07K 2317/92* (2013.01); *C07K 2319/00* (2013.01); *C07K 2319/70* (2013.01); *C12N 2770/20033* (2013.01); *G01N 2333/165* (2013.01); *G01N 2469/10* (2013.01)

(58) Field of Classification Search
None
See application file for complete search history.

(56) References Cited

FOREIGN PATENT DOCUMENTS

| CN | 103864924 A | 6/2014 |
|---|---|---|
| WO | WO 2014/045254 A2 | 3/2014 |
| WO | WO 2014/134439 A1 | 9/2014 |

OTHER PUBLICATIONS

Paul. Fundamental Immunology, 3rd Edition, Raven Press, New York, Chapter 8, pp. 292-295, 1993 (Year: 1993).*
MacCallum et al. Antibody-antigen Interactions: Contact Analysis and Binding Site Topography. Journal of Molecular Biology, 262: 732-745,1996 (Year: 1996).*
Casset et al. A peptide mimetic of an anti-CD4 monoclonal antibody by rational design. Biochemical and Biophysical Research Communications, 307:198-205, 2003 (Year: 2003).*
Vajdos et al. Comprehensive Functional Maps of the Antigenbinding Site of an Anti-ErbB2 Antibody Obtained with Shotgun Scanning Mutagenesis. Journal of Molecular Biology, Jul. 5, 2002;320(2):415-28 (Year: 2002).*
Brown et al. Tolerance to Single, but Not Multiple, Amino Acid Replacements in Antibody VH CDR2. Journal of Immunology. May 1996; 156(9):3285-91 (Year: 1996).*
Rudikoff et al. Single amino acid substitution altering antigen-binding specificity. Proc. Natl. Acad. Sci. USA, 79(6):1979-1983, Mar. 1982 (Year: 1982).*
Colman. Effects of amino acid sequence changes on antibody-antigen interactions. Research in Immunology, 145:33-36, 1994 (Year: 1994).*
Gussow et al. Humanization of monoclonal antibodies.1991, Methods in Enzymology 203:99-121 (Year: 1991).*

(Continued)

*Primary Examiner* — Vanessa L. Ford
*Assistant Examiner* — Sandra E Dillahunt
(74) *Attorney, Agent, or Firm* — Leydig, Voit & Mayer, Ltd.

(57) ABSTRACT

The invention provides polypeptides (e.g., antibodies) and fusion proteins that target a epitope in the receptor binding domain (RBD) of the spike (S) glycoprotein of the Middle East Respiratory Syndrome Coronavirus (MERS-CoV). The polypeptides and fusion proteins can be used to treat and prevent MERS-CoV infection in mammals.

Figure 2:
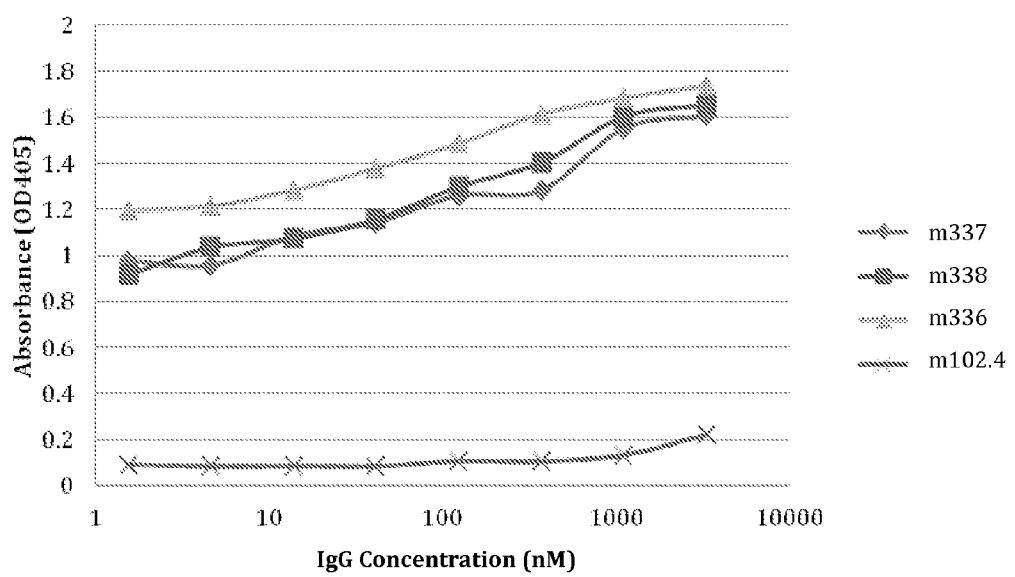

20 Claims, 3 Drawing Sheets
Specification includes a Sequence Listing.

(56) References Cited

OTHER PUBLICATIONS

Falzarano et al., "Interferon-α2b and ribavirin treatment improves outcome in MERS-CoV-infected rhesus macaques," *Nat. Med.*, 19 (10), 1313-1317 (2013) author manuscript.

International Preliminary Report on Patentability, Application No. PCT/US2014/060863, dated Apr. 19, 2016.

International Search Report, Application No. PCT/US2014/060863, dated Feb. 2, 2015.

Jiang et al., "Potent neutralization of MERS-CoV by human neutralizing monoclonal antibodies to the viral spike glycoprotein," *Sci. Transl. Med.*, 6 (234), 234ra59 (2014).

Lu et al., "Molecular basis of binding between novel human coronavirus MERS-CoV and its receptor CD26," *Nature*, 500 (7461), 227-231 (2013).

Momattin et al., "Therapeutic options for Middle East respiratory syndrome coronavirus (MERS-CoV)—possible lessons from a systematic review of SARS-CoV therapy," *Int. J. Infect. Dis.*, 17 (10), e792-e798 (2013).

Mou et al., "The receptor binding domain of the new Middle East respiratory syndrome coronavirus maps to a 231-residue region in the spike protein that efficiently elicits neutralizing antibodies," *J. Virol.*, 87 (16), 9379-9383 (2013).

Tang et al., "Identification of human neutralizing antibodies against MERS-CoV and their role in virus adaptive evolution," *Proc. Natl. Acad. Sci. U.S.A.*, 111 (19), E2018-E2026 (2014).

Written Opinion of the International Searching Authority, Application No. PCT/US2014/060863, dated Feb. 2, 2015.

Ying et al., "Exceptionally potent neutralizalion of Middle East respiratory syndrome coronavirus by human monoclonal antibodies," *J. Virol.*, 88 (14), 7796-7805 (2014).

Zaki et al., "Isolation of a novel coronavirus from a man with pneumonia in Saudi Arabia" *N. Engl. J. Med.*, 367 (19), 1814-1820 (2012).

Zhu et al., "Human monoclonal antibodies as candidate therapeutics against emerging viruses and HIV-1," *Virol. Sin.*, 28 (2), 71-80 (2013).

* cited by examiner

FIG. 1

FIG. 3

HUMAN MONOCLONAL ANTIBODIES AGAINST THE MIDDLE EAST RESPIRATORY SYNDROME CORONAVIRUS (MERS-COV) AND ENGINEERED BISPECIFIC FUSIONS WITH INHIBITORY PEPTIDES

CROSS-REFERENCE TO RELATED APPLICATIONS

This patent application is the U.S. national phase of PCT/US2014/060863, filed Oct. 16, 2014, which claims the benefit of U.S. Provisional Patent Application No. 61/892,750, filed Oct. 18, 2013, which applications are incorporated by reference.

STATEMENT REGARDING FEDERALLY SPONSORED RESEARCH OR DEVELOPMENT

This invention was made with Government support under project number 1ZIABC011156-09 by the National Institutes of Health, National Cancer Institute. The Government has certain rights in the invention.

Incorporated by reference in its entirety herein is a computer-readable nucleotide/amino acid sequence listing submitted concurrently herewith and identified as follows: One 27,076 Byte ANSI (Text) file named "723556_ST25.txt" created on Apr. 18, 2016.

BACKGROUND OF THE INVENTION

Emerging viruses present a serious threat to human health and safety. In the past few decades, many infectious diseases, such as those caused by the human immunodeficiency virus (HIV), Ebola virus (EBOV), Nipah (NiV), and Hendra (HeV) viruses, have effectively made the jump from animal to human hosts and devastated entire populations and economies.

In 2012, a novel human coronavirus, the Middle East Respiratory Syndrome Coronavirus (MERS-CoV), was isolated from a Saudi Arabian patient suffering from severe pneumonia who later died of respiratory and renal failure (see Zaki et al., *N Engl. J. Med.*, 367: 1814-1820 (2012)). Like other coronaviruses, the MERS-CoV virion utilizes a large surface spike (S) glycoprotein for interaction with and entry into the target cell. The S glycoprotein consists of a globular S1 domain at the N-terminal region, followed by membrane-proximal S2 domain, a transmembrane domain and an intracellular domain. Determinants of cellular tropism and interaction with the target cell are within the S1 domain, while mediators of membrane fusion have been identified within the S2 domain. Through co-purification with the MERS-CoV S1 domain, dipeptidyl peptidase 4 (DPP4, also called CD26) was identified as cellular receptor for MERS-CoV. DDP4 is expressed on the surface of several cell types, including those found in human airways, and possesses ectopeptidase activity, although this enzymatic function does not appear to be essential for viral entry.

To date, MERS-CoV has infected 130 humans from the Middle East to Western Europe with a high mortality rate killing at least 58 humans. MERS-CoV is able to transmit from human to human.

The severity of diseases and high mortality caused by MERS-CoV and the possibility of human-to-human transmission pose a serious threat to public health and urgently require the development of therapeutics and vaccines.

Currently there are no effective therapeutics against MERS-CoV. In September 2013, a report was published describing reduction of MERS-CoV replication and improvement of clinical outcome in rhesus macaques treated with IFN-α2b and ribavirin, which may work primarily by reducing damaging inflammation of the lung and promoting healing by altering the host response, rather than directly targeting the virus (see Falzarano et al., *Nature Medicine*, 9: 1313-1317 (2013)). However, the treatment was initiated soon (8 hours) after challenge and the disease in the macaques was at best mild to moderate in severity, so whether the drug cocktail would work when faced with severe human disease, which may take longer to develop, remains unclear. In addition, the same two-drug combination has already been used on MERS-CoV patients in Saudi Arabia with less-than-positive results, according to the country's deputy health minister, Doctor Ziad A. Memish, although the drugs were supplied at too late a stage (see Momattin et al., *Int. J. Infect. Dis.*, 17(1): e792-798 (October 2013)). There are no targeted therapies available against the MERS-CoV.

There is a desire for the development of therapeutics and vaccines against MERS-CoV.

BRIEF SUMMARY OF THE INVENTION

The invention provides a polypeptide comprising (a) the amino acid sequences of SEQ ID NOs: 3-8; (b) the amino acid sequences of SEQ ID NOs: 4 and 11-15; or (c) the amino acid sequences of SEQ ID NOs: 11 and 18-22. Nucleic acids (e.g., in the form of a vector) encoding the polypeptide (e.g., antibody), as well as compositions or cells comprising the polypeptide, fusion proteins, or nucleic acids also are provided.

The invention additionally provides a method of inhibiting a MERS-CoV infection in a cell or a host comprising administering the polypeptide (e.g., antibody) or fusion protein to the cell or host, such that the MERS-CoV infection is inhibited.

BRIEF DESCRIPTION OF THE SEVERAL VIEWS OF THE DRAWING(S)

Figure 1:
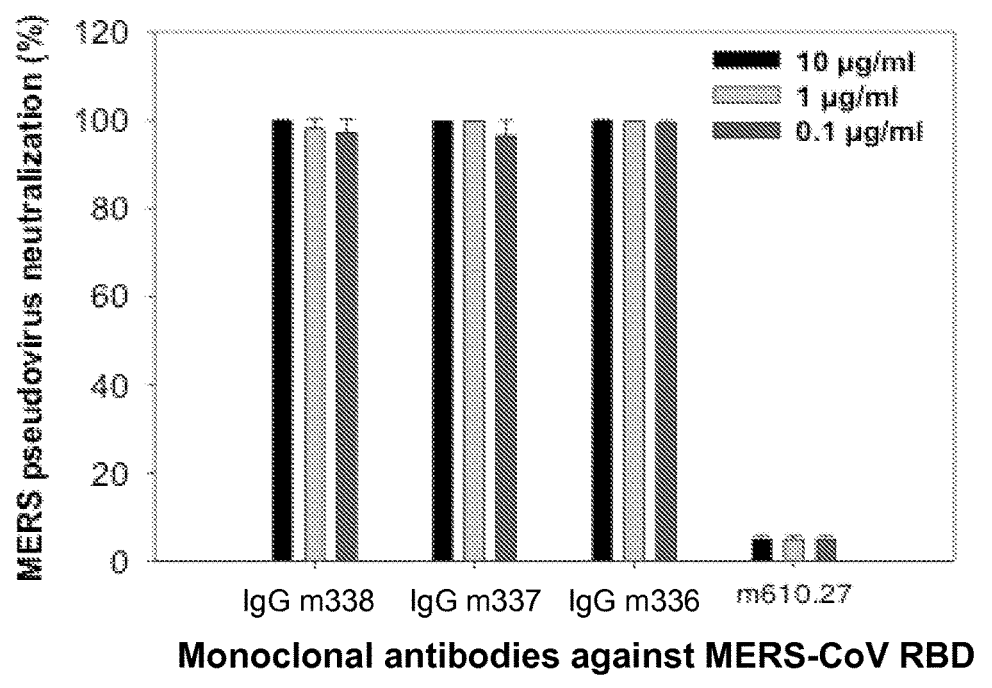

FIG. 1 is a graph demonstrating inhibition of pseudovirus MERS-CoV infection by IgGs m336, m337 and m338. The m610.27 antibody, which is specific for IGF2, was used as the negative control. MERS-CoV pseudovirus neutralization (%) is indicated on the y-axis, and the particular monoclonal antibody (at concentrations of 10 µg/ml, 1 µg/ml, and 0.1 µg/ml) is indicated on the x-axis.

FIG. 2 is a graph demonstrating the binding of IgG1s to the MERS CoV RBD as measured by ELISA. The absorbance (optical density) at 405 nm is indicated on the y-axis, and the IgG concentration (nM) is indicated on the x-axis.

Figure 3:
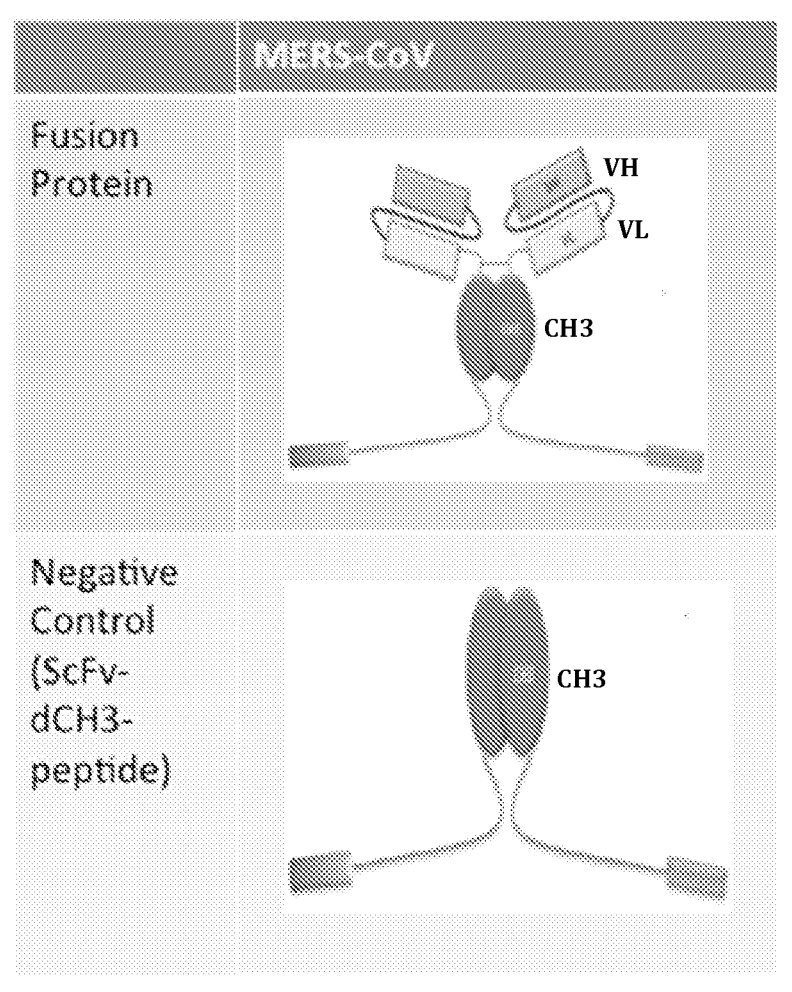

FIG. 3 is a schematic of an anti-MERS-CoV fusion protein construct with its negative control (ScFv-dCH3-peptide). VH and VL denote variable heavy and light chains, respectively, composing a scFv. The CH3 is an antibody dimerization domain. The anti-MERS-CoV fusion protein construct and its respective control (right upper and lower panels, respectively) contain a non-cleavable linker that connects the CH3 with the inhibitory peptide (indicated with a rectangle shape at the bottom of the figure).

DETAILED DESCRIPTION OF THE INVENTION

The invention provides polypeptides (e.g., antibodies) that bind with an epitope of the MERS-CoV receptor binding domain (RBD) of MERS-CoV spike (S) protein.

The polypeptide can be any suitable polypeptide. The polypeptide preferably is an antibody.

In a first embodiment, the polypeptide (e.g., antibody) can comprise one or more (e.g., two, three, four, five, or six) complementarity determining regions (CDRs) of the m336 antibody, wherein the CDRs correspond to the amino acid sequences of SEQ ID NO: 3 (HCDR1), SEQ ID NO: 4 (HCDR2), SEQ ID NO: 5 (HCDR3), SEQ ID NO: 6 (LCDR1), SEQ ID NO: 7 (LCDR2), and SEQ ID NO: 8 (LCDR3). The polypeptide (e.g., antibody) can comprise one or both of the heavy and light chains of the m336 antibody, which correspond to the amino acid sequences of SEQ ID NO: 1 and SEQ ID NO: 2, respectively.

In a second embodiment, the polypeptide (e.g., antibody) can comprise one or more (e.g., two, three, four, five, or six) CDRs of the m337 antibody, wherein the CDRs correspond to the amino acid sequences of SEQ ID NO: 11 (HCDR1), SEQ ID NO: 4 (HCDR2), SEQ ID NO: 12 (HCDR3), SEQ ID NO: 13 (LCDR1), SEQ ID NO: 14 (LCDR2), and SEQ ID NO: 15 (LCDR3). The polypeptide (e.g., antibody) can comprise one or both of the heavy and light chains of the m337 antibody, which correspond to the amino acid sequences of SEQ ID NO: 9 and SEQ ID NO: 10, respectively.

In a third embodiment, the polypeptide (e.g., antibody) can comprise one or more (e.g., two, three, four, five, or six) CDRs of the m338 antibody, wherein the CDRs correspond to the amino acid sequences of SEQ ID NO: 11 (HCDR1), SEQ ID NO: 18 (HCDR2), SEQ ID NO: 19 (HCDR3), SEQ ID NO: 20 (LCDR1), SEQ ID NO: 21 (LCDR2), and SEQ ID NO: 22 (LCDR3). The polypeptide (e.g., antibody) can comprise one or both of the heavy and light chains of the m338 antibody, which correspond to the amino acid sequences of SEQ ID NO: 16 and SEQ ID NO: 17, respectively.

Antibodies of the invention include both polyclonal and monoclonal antibodies. In addition to intact immunoglobulin molecules, also included are fragments or polymers of those immunoglobulin molecules, and human or humanized versions of immunoglobulin molecules or fragments thereof, as long as the molecules maintain the ability to bind with an epitope of the MERS-CoV RBD. The antibodies can be tested for their desired activity using the in vitro assays described herein, or by analogous methods, after which their in vivo therapeutic and/or prophylactic activities can be confirmed and quantified according to known clinical testing methods.

In a preferred embodiment, the polypeptide is a monoclonal antibody or fragment thereof. A monoclonal antibody refers to an antibody where the individual antibody within a population is identical. The monoclonal antibodies of the invention specifically include chimeric antibodies, in which a portion of the heavy and/or light chain is identical with, or homologous to, corresponding sequences in antibodies derived from a particular species or belonging to a particular antibody class or subclass, while the remainder of the chain(s) is identical with, or homologous to, corresponding sequences in antibodies derived from another species or belonging to another antibody class or subclass, as well as fragments of such antibodies, as long as they exhibit the desired antagonistic activity (see, e.g., U.S. Pat. No. 4,816,567 and Morrison et al., *PNAS*, 81: 6851-6855 (1984)).

The monoclonal antibodies can be made using any procedure known in the art. For example, monoclonal antibodies of the invention can be prepared using hybridoma methods, such as those described by Kohler et al., *Nature*, 256: 495-497 (1975).

The monoclonal antibodies also can be made by recombinant DNA methods, such as those described in U.S. Pat. No. 4,816,567. DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 and 6,096,441.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in International Patent Application WO 94/29348 and U.S. Pat. No. 4,342,566. Papain digestion of antibodies typically produces two identical antigen-binding fragments, called Fab fragments, each with a single antigen binding site, and a residual Fc fragment. Pepsin treatment yields a fragment that has two antigen combining sites and is still capable of cross-linking antigen.

The invention encompasses chimeric antibodies and hybrid antibodies, with dual or multiple antigen or epitope specificities, single chain antibodies and fragments, such as, Fab', F(ab')$_2$, Fab, scFv, di-scFv, and the like, including hybrid fragments and IgGs. The invention also encompasses engineered antibody domains (eAds), which are also known as single-domain antibodies (a.k.a. "domain antibodies" ("dAbs"). Such antibodies and fragments can be made by techniques known in the art and can be screened for specificity and activity according to the methods set forth in the Examples and in general methods for producing antibodies and screening antibodies for specificity and activity (see, e.g., Harlow and Lane. *Antibodies, A Laboratory Manual.* Cold Spring Harbor Publications, New York, (1988)).

The invention also encompasses human antibodies and/or humanized antibodies. Many non-human antibodies (e.g., those derived from mice, rats, or rabbits) are naturally antigenic in humans and, thus, can give rise to undesirable immune responses when administered to humans. Therefore, the use of human or humanized antibodies in the methods of the invention serves to lessen the chance that an antibody administered to a human will evoke an undesirable immune response.

The human antibodies and humanized antibodies of the invention can be prepared by any known technique. Examples of techniques for human monoclonal antibody production include those described by Boerner et al., *J. Immunol.*, 147(1): 86-95 (1991). Human antibodies of the invention (and fragments thereof) can also be produced using phage display libraries (see, e.g., Marks et al., *J. Mol. Biol.*, 222: 581-597 (1991)). The human antibodies of the invention can also be obtained from transgenic animals. For example, transgenic, mutant mice that are capable of producing a full repertoire of human antibodies, in response to immunization, have been described (see, e.g., Jakobovits et al., *PNAS*, 90: 2551-255 (1993); and Jakobovits et al., *Nature*, 362: 255-258 (1993)).

Methods for humanizing non-human antibodies are well known in the art. For example, humanized antibodies can be generated according to the methods disclosed in Jones et al., *Nature*, 321: 522-525 (1986); Riechmann et al., *Nature*, 332: 323-327 (1988); Verhoeyen et al., *Science*, 239, 1534-1536 (1988), by substituting rodent complementarity-determining regions (CDRs) or CDR sequences for the corresponding sequences of a human antibody. Methods that can be used to produce humanized antibodies are also described in U.S. Pat. Nos. 4,816,567, 5,565,332, 5,721,367, 5,837,243, 5,939,598, 6,130,364, and 6,180,377.

The polypeptides of the invention also encompass bivalent antibodies, as well as fusion molecules and conjugates with other molecules that can enhance the MERS-CoV inhibitory effect of the polypeptide. The generation of fusion molecules (e.g., proteins) and conjugates (e.g., through physical or chemical conjugation) is within the ordinary skill in the art and can involve the use of restriction enzyme or recombinational cloning techniques (see, e.g., U.S. Pat. No. 5,314,995).

The fusion partner can be any suitable moiety that does not substantially inhibit the polypeptide's ability to bind its target. Desirably, the fusion partner enhances the stability and/or potency of the fusion protein as compared to the stability or potency of the polypeptide (antibody) in the absence of the fusion partner. For instance, the fusion partner can be a naturally occurring protein or fragment thereof that resists degradation or removal by endogenous mechanisms in vivo, thereby increasing the half-life of the fusion protein as compared to the polypeptide (antibody) in the absence of the fusion partner. Examples of suitable fusion partners include: (a) proteins from the extracellular matrix, such as collagen, laminin, integrin, and fibronectin; (b) proteins found in blood, such as serum albumin, serum albumin-binding peptide (SAbp), fibrinogen A, fibrinogen B, serum amyloid protein A, heptaglobin, protein, ubiquitin, uteroglobulin, β-2 microglobulin, plasminogen, lysozyme, cystatin C, α-1-antitrypsin, and pancreatic kypsin inhibitor; (c) immune serum proteins, such as IgE, IgG, IgM, and their fragments (e.g., Fe); (d) transport proteins, such as retinol binding protein; (e) defensins, such as β-defensin 1, neutrophil defensins 1, 2 and 3; (f) proteins found at the blood brain barrier or in neural tissues, such as melanocortin receptor, myelin, ascorbate transporter; (g) transferrin receptor specific ligand-neurophaimaceutical agent fusion proteins, brain capillary endothelial cell receptor, transferrin, transferrin receptor, insulin, insulin-like growth factor 1 (IGF 1) receptor, insulin-like growth factor 2 (IGF 2) receptor, insulin receptor; (h) proteins localized to the kidney, such as polycystin, type IV collagen, organic anion transporter K1, Heymann's antigen; (i) proteins localized to the liver, such as alcohol dehydrogenase, G250; (j) blood coagulation factor X; (k) α-1 antitrypsin; (l) HNF 1 α; (m) proteins localized to the lung, such as secretory component; (n) proteins localized to the heart, such as HSP 27; (o) proteins localized to the skin, such as keratin; (p) bone specific proteins, such as bone morphogenic proteins (BMPs), for example, BMP-2, -4, -5, -6, -7 (also referred to as osteogenic protein (OP-I) and -8 (OP-2); (q) tumor specific proteins, such as human trophoblast antigen, herceptin receptor, estrogen receptor, cathepsins, for example, cathepsin B (found in liver and spleen); (r) disease-specific proteins, such as antigens expressed only on activated T-cells: including LAG-3 (lymphocyte activation gene); osteoprotegerin ligand (OPGL); OX40; metalloproteases, including CG6512 Drosophila, human paraplegin, human FtsH, human AFG3L2, murine ftsH; angiogenic growth factors, including acidic fibroblast growth factor (FGF-I), basic fibroblast growth factor (FGF-2), Vascular endothelial growth factor/vascular permeability factor (VEGF/VPF), transforming growth factor-α (TGF-α), tumor necrosis factor-alpha (TNF-α), angiogenin, interleukin-3 (IL-3), interleukin-8 (IL-8), platelet derived endothelial growth factor (PD-ECGF), placental growth factor (PlGF), midkine platelet-derived growth factor-BB (PDGF), fractalkine; (s) stress proteins (heat shock proteins); and (t) proteins involved in Fc transport.

In one embodiment, the fusion protein comprises an inhibitory peptide, such as an inhibitory peptide that binds to membrane fusion intermediates. An example of an inhibitory peptide that can be included in the fusion protein includes the amino acid sequence of SEQ ID NO: 26. Additionally or alternatively, the fusion protein comprises a CH3 antibody dimerization domain sequence. Any CH3 antibody dimerization domain sequence can be included in the fusion protein. An example of a CH3 antibody dimerization domain sequence is the amino acid sequence of SEQ ID NO: 27.

The fusion protein can comprise more than one fusion partner. Thus, in a related aspect, the fusion protein comprises two or more different fusion partners.

The polypeptide (antibody) and one or more fusion partners can be joined via a linker (i.e., a flexible molecular connection, such as a flexible polypeptide chain). The linker can be any suitable linker, such that the fusion protein can bind to the epitope of the RBD (i.e., the fusion protein is not excluded from binding by molecular steric hindrance). The linker can be any suitable length, but is preferably at least about 15 (e.g., at least about 20, at least about 25, at least about 30, at least about 35, at least about 40, at least about 45, at least about 50, or ranges thereof) amino acids in length. In one embodiment, the linker is a flexible non-cleavable linker. An example of a suitable linker includes, but is not limited to, $(G_4S)_3$ (SEQ ID NO: 28).

For instance, the fusion protein can comprise an anti-MERS-CoV antibody (e.g., an scFv or eAd), a CH3 antibody dimerization domain sequence, and an inhibitory peptide, wherein the CH3 antibody dimerization domain and the inhibitory peptide are joined by a flexible non-cleavable linker. In one embodiment, the fusion protein can have the following configuration: scFv-CH3-linker-inhibitory peptide. In a particular embodiment, the fusion protein comprises the amino acid sequence of SEQ ID NO: 23, which fusion protein has the following configuration: m336 scFv-CH3-linker-inhibitory peptide.

The polypeptides (antibodies) or fusion proteins can be PEGylated, or coupled to polymers of similar structure, function and purpose, to confer enhanced stability and half-life. PEGylation can provide increased half-life and resistance to degradation without a loss in activity (e.g., binding affinity) relative to non-PEGylated antibody polypeptides. Since PEGylation may not be advantageous with respect to some targets, in particular, those epitopes which are sterically-obstructed, the polypeptide (antibody) should be minimally PEGylated so as not to negatively impact the accessibility of the polypeptide (antibody) to the size-restricted antigen. The polypeptides (antibodies) or fusion proteins can be coupled to PEG or PEG-like polymers by any suitable means known in the art. Suitable PEG or PEG-like moieties can be synthetic or naturally occurring and include, but are not limited to, straight or branched chain polyalkylene, polyalkenylene or polyoxyalkylene polymers, or a branched or unbranched polysaccharide, such as a homo- or heteropolysaccharide. Preferred examples of synthetic polymers include straight or branched chain poly (ethylene glycol) (PEG), poly(propylene glycol), or poly (vinyl alcohol) and derivatives or substituted forms thereof Substituted polymers for linkage to the domain antibodies also include substituted PEG, including methoxy(polyethylene glycol). Naturally occurring polymer moieties which can be used in addition to or in place of PEG include, for example, lactose, amylose, dextran, or glycogen, as well as derivatives thereof.

The polypeptides (antibodies) or fusion proteins can be multimerized, as for example, hetero- or homodimers, hetero- or homotrimers, hetero- or homotetramers, or higher order hetero- or homomultimers. Multimerization can increase the strength of antigen binding, wherein the strength of binding is related to the sum of the binding affinities of the multiple binding sites. In particular, cysteine residue(s) can be introduced in the amino acid sequence of the polypeptides (antibodies) or fusion protein, thereby allowing interchain disulfide bond formation in a multimerized form of the antibodies. The homodimeric or heterodimeric (or multimeric) antibodies or fusion proteins can include combinations of the same polypeptide (antibody) chains or different polypeptide (antibody) chains, such that more than one epitope is targeted at a time by the same construct. Such epitopes can be proximally located in the target (e.g., on the MERS-CoV target) such that the binding of one epitope facilitates the binding of the multimeric antibody of the invention to the second or more epitopes. The epitopes targeted by multimeric antibodies also can be distally situated.

Conjugates comprising the polypeptides (antibodies) or fusion proteins of the invention conjugated to cytotoxic agents, such as chemotherapeutic agents, toxin (e.g., an enzymatically active toxin of bacterial, fungal, plant or animal origin, or fragments thereof), radioactive isotopes (i.e., a radioconjugate), or antiviral compounds also are encompassed by the invention. Alternatively, the polypeptides (antibodies) or fusion proteins can be co-administered with the cytotoxic agents, antiviral compounds, and the like.

Methods for conjugating the polypeptides (antibodies) or fusion proteins to the cytotoxic agents, chemotherapeutic agents, toxins, antibacterial compounds, and antiviral compounds, and the like are well known in the art. For example, conjugates can be made using a variety of bifunctional protein coupling agents such as N-succinimidyl-3-(2-pyridyidithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as his (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Detectable agents, such as fluorescent compounds, also can be added to the polypeptides (antibodies) or fusion proteins. Exemplary fluorescent detectable agents include fluorescein, fluorescein isothiocyanate, rhodamine, 5-dimethylamine-l-napthalenesulfonyl chloride, phycoerythrin and the like. The domain antibodies or fusion proteins also can be derivatized with detectable enzymes, such as alkaline phosphatase, horseradish peroxidase, glucose oxidase and the like. When the polypeptide (antibody) or fusion protein construct is derivatized with a detectable enzyme, it is detected by adding additional reagents that the enzyme uses to produce a detectable reaction product. The polypeptide (antibody) or fusion protein construct also can be derivatized with biotin, and detected through indirect measurement of avidin or streptavidin binding.

Additional peptide sequences can be added to the polypeptides (antibodies) or fusion proteins, which act to promote stability, purification, and/or detection. For example, a reporter peptide portion (e.g., green fluorescent protein (GFP), (β-galactosidase, or a detectable domain thereof) can be used. Purification-facilitating peptide sequences include those derived or obtained from maltose binding protein (MBP), glutathione-S-transferase (GST), or thioredoxin (TRX). The polypeptide (antibody) or fusion protein also or alternatively can be tagged with an epitope which can be antibody purified (e.g., the Flag epitope, which is commercially available from Kodak (New Haven, Conn.)), a hexa-histidine peptide, such as the tag provided in a pQE vector available from QIAGEN, Inc. (Chatsworth, Calif.), or an HA tag (as described in, e.g., Wilson et al., *Cell,* 37, 767 (1984)).

Additional fusion partners for use in connection herewith are described in WO 2009/089295.

The polypeptides (antibodies) or fusion proteins can be prepared by any suitable method. For example, the polypeptides (antibodies) and fusion proteins can be prepared by synthesizing the amino acid sequence or by expressing a nucleic acid encoding the amino acid sequence in a cell and harvesting the resulting polypeptide (antibody) or fusion protein from the cell. A combination of such methods also can be used. Methods of de novo synthesizing peptides and methods of recombinantly producing peptides are known in the art (see, e.g., Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; Sambrook et al., *Molecular Cloning: A Laboratory Manual,* 3rd ed., Cold Spring Harbor Press, Cold Spring Harbor, N.Y. 2001; and Ausubel et al., *Current Protocols in Molecular Biology*, Greene Publishing Associates and John Wiley & Sons, NY, 1994).

The invention also provides a nucleic acid molecule comprising a non-genomic nucleic acid sequence (e.g., cDNA) encoding the amino acid sequence of the polypeptide (antibody) or fusion protein. The nucleic acid can comprise DNA or RNA, and can be single or double stranded. Furthermore, the nucleic acid can comprise nucleotide analogues or derivatives (e.g., inosine or phophorothioate nucleotides and the like).

The nucleic acid can be provided as part of a construct comprising the nucleic acid and elements that enable delivery of the nucleic acid to a cell, and/or expression of the nucleic acid in a cell. Such elements include, for example, expression vectors, promoters, and transcription and/or translation sequences. Suitable vectors, promoters, transcription/translation sequences, and other elements, as well as methods of preparing such nucleic acids and constructs, are known in the art (e.g., Sambrook et al., supra; and Ausubel et al., supra).

The invention further provides a vector comprising the nucleic acid. Examples of suitable vectors include plasmids (e.g., DNA plasmids), yeast (e.g., *Saccharomyces*), and viral vectors, such as poxvirus, retrovirus, adenovirus, adeno-associated virus, herpes virus, polio virus, alphavirus, baculorvirus, and Sindbis virus. When the vector is a plasmid (e.g. DNA plasmid), the plasmid can be complexed with chitosan.

When the vector is for administration to a host (e.g., human), the vector preferably has a low replicative efficiency in a target cell (e.g., no more than about 1 progeny per cell or, more preferably, no more than 0.1 progeny per cell are produced). Replication efficiency can readily be determined empirically by determining the virus titer after infection of the target cell.

The polypeptide (antibody), fusion protein, or conjugate can be administered to a mammal in the form of a cell comprising a nucleic acid encoding the polypeptide (antibody) or fusion protein, optionally in the faun of a vector. Thus, the invention also provides a cell comprising a vector or nucleic acid encoding the polypeptide (antibody) or fusion protein from which the polypeptide (antibody) or fusion protein desirably is secreted. Any suitable cell can be used. Examples include host cells, such as *E. coli* (e.g., *E. coli* Tb-1, TG-2, DH5α, XL-Blue MRF' (Stratagene), SA2821, and Y1090), *Bacillus subtilis, Salmonella typhimurium, Serratia marcescens*, Pseudomonas (e.g., *P. aerugenosa*), *N. grassa*, insect cells (e.g., Sf9, Ea4), yeast (*S. cerevisiae*) cells, and cells derived from a mammal, including human cell lines. Specific examples of suitable eukaryotic cells include VERO, HeLa, 3T3, Chinese hamster ovary (CHO) cells, W138 BHK, COS-7, and MDCK cells. Alternatively and preferably, cells from a mammal, such as a human, to be treated in accordance with the methods described herein can be used as host cells. In one embodiment, the cell is a human B cell.

Methods of introducing vectors into isolated host cells and the culture and selection of transformed host cells in vitro are known in the art and include the use of calcium chloride-mediated transformation, transduction, conjugation, triparental mating, DEAE, dextran-mediated transfection, infection, membrane fusion with liposomes, high velocity bombardment with DNA-coated microprojectiles, direct microinjection into single cells, and electroporation (see, e.g., Sambrook et al., supra, Davis et al., *Basic Methods in Molecular Biology* (1986), and Neumann et al., *EMBO J.* 1, 841 (1982)). Desirably, the cell comprising the vector or nucleic acid expresses the nucleic acid encoding the polypeptide (antibody) or fusion protein such that the nucleic acid sequence is transcribed and translated efficiently by the cell.

The polypeptide (antibody), fusion protein, conjugate, nucleic acid, vector, or cell can be isolated. The term "isolated" as used herein encompasses compounds or compositions that have been removed from a biological environment (e.g., a cell, tissue, culture medium, body fluid, etc.) or otherwise increased in purity to any degree (e.g., isolated from a synthesis medium). Isolated compounds and compositions, thus, can be synthetic or naturally produced.

The polypeptide (antibody), fusion protein, conjugate, nucleic acid, vector, or cell can be administered to any host (e.g., mammal, preferably a human) in need thereof. As a result of administration of the polypeptide (antibody), fusion protein, conjugate, nucleic acid, vector, or cell to the mammal, infection of the mammal by MERS-CoV is inhibited. The inventive method can prophylactically or therapeutically inhibit infection by MERS-CoV.

When provided therapeutically, the polypeptide (antibody), fusion protein, conjugate, nucleic acid, vector, cell, or composition thereof is provided at or after the diagnosis of MERS-CoV infection.

When provided prophylactically, the polypeptide (antibody), fusion protein, conjugate, nucleic acid, vector, cell, or composition thereof is provided in advance of MERS-CoV infection, such as to patients or subjects who are at risk for being exposed to MERS-CoV or who have been newly exposed to MERS-CoV, such as healthcare workers, blood products, or transplantation tissue, and other individuals who have been exposed to a body fluid that contains or may contain MERS-CoV. The prophylactic administration of the polypeptide (antibody), fusion protein, conjugate, nucleic acid, vector, cell, or composition thereof prevents, ameliorates, or delays MERS-CoV infection. In subjects who have been newly exposed to MERS-CoV but who have not yet displayed the presence of the virus (as measured by PCR or other assays for detecting the virus) in blood or other body fluid, efficacious treatment with the polypeptide (antibody), fusion protein, conjugate, nucleic acid, vector, cell, or composition thereof partially or completely inhibits or delays the appearance of the virus or minimizes the level of the virus in the blood or other body fluid of the exposed individual.

The efficacy of the polypeptide (antibody), fusion protein, conjugate, nucleic acid, vector, cell, or composition thereof can be assessed in various ways well known to the skilled practitioner. For instance, one of ordinary skill in the art will understand that an antibody of the invention is efficacious in treating or inhibiting a MERS-CoV infection in a subject by observing that the antibody reduces viral load or delays or prevents a further increase in viral load. Viral loads can be measured by methods that are known in the art, for example, using PCR assays to detect the presence of MERS-CoV nucleic acid or antibody assays to detect the presence of MERS-CoV protein in a sample (e.g., blood or another body fluid) from a subject or patient, or by measuring the level of circulating anti-MERS-CoV antibodies in the patient.

The polypeptide (antibody), fusion protein, conjugate, nucleic acid, vector, or cell can be formulated as a composition (e.g., pharmaceutical composition) comprising the polypeptide (antibody), fusion protein, conjugate, nucleic acid, vector, or cell and a carrier (e.g., a pharmaceutically or physiologically acceptable carrier). Furthermore, polypeptide (antibody), fusion protein, conjugate, nucleic acid, vector, cell, or composition of the invention can be used in the methods described herein alone or as part of a pharmaceutical formulation.

Compositions (e.g., pharmaceutical compositions) comprising the polypeptide (antibody), fusion protein, conjugate, nucleic acid, vector, or cell can include carriers, thickeners, diluents, buffers, preservatives, surface active agents and the like.

Suitable carriers and their formulations are described in A. R. Gennaro, ed., *Remington: The Science and Practice of Pharmacy* (19th ed.), Mack Publishing Company, Easton, PA (1995). Pharmaceutical carriers, include sterile water, saline, Ringer's solution, dextrose solution, and buffered solutions at physiological pH. Typically, an appropriate amount of a pharmaceutically acceptable salt is used in the formulation to render the formulation isotonic. The pH of the formulation is preferably from about 5 to about 8 (e.g., about 5.5, about 6, about 6.5, about 7, about 7.5, and ranges thereof). More preferably, the pH is about 7 to about 7.5. Further carriers include sustained-release preparations, such as semipermeable matrices of solid hydrophobic polymers containing the fusion protein, which matrices are in the form of shaped articles (e.g., films, liposomes, or microparticles). It will be apparent to those persons skilled in the art that certain carriers may be more preferable depending upon, for instance, the route of administration and concentration of composition being administered.

The composition (e.g., pharmaceutical composition) can comprise more than one polypeptide (antibody), fusion protein, conjugate, nucleic acid, vector, or cell of the invention. Alternatively, or in addition, the composition can comprise one or more other pharmaceutically active agents or drugs. Examples of such other pharmaceutically active agents or drugs that may be suitable for use in the pharmaceutical composition include anticancer agents (e.g., chemotherapeutic drugs), antibiotics, antiviral drugs, antifungal drugs, cyclophosphamide, and combinations thereof. Suitable antiviral agents include, but are not limited to, ribavirin. In one embodiment, the composition can comprise one or more polypeptide (antibody), fusion protein, conjugate, nucleic acid, vector, or cell of the invention and one or more other pharmaceutically active agents or drugs (e.g., ribavirin and/or interferon (IFN)-α2β as described in Falzarano et al., *Nature Medicine,* 9: 1313-1317 (2013)).

Suitable methods of administering a polypeptide (antibody), fusion protein, conjugate, nucleic acid, vector, cell, or composition thereof to hosts are known in the art. The host can be any suitable host, such as a mammal (e.g., a rodent, such as a mouse, rat, hamster, or guinea pig, rabbit, cat, dog, pig, goat, cow, horse, primate, or human).

Administration can be topical (including ophthalmical, vaginal, rectal, intranasal, transdermal, and the like), oral, by inhalation, or parenteral (including by intravenous drip or subcutaneous, intracavity, intraperitoneal, or intramuscular injection). Topical intranasal administration refers to the delivery of the compositions into the nose and nasal passages through one or both of the nares and can comprise delivery by a spraying mechanism or droplet mechanism, or through aerosolization of the nucleic acid, vector, or fusion protein. Administration of the compositions by inhalant can be through the nose or mouth via delivery by a spraying or droplet mechanism. Delivery can also be directly to any area of the respiratory system (e.g., lungs) via intubation.

Formulations for topical administration include ointments, lotions, creams, gels, drops, suppositories, sprays, liquids, and powders. Conventional pharmaceutical carriers, aqueous, powder, or oily bases, thickeners, and the like may be necessary or desirable.

If the composition is to be administered parenterally, the administration is generally by injection. Injectables can be prepared in conventional forms, either as liquid solutions or suspensions, solid forms suitable for suspension in liquid prior to injection, or as emulsions. Additionally, parental administration can involve the preparation of a slow-release or sustained-release system, such that a constant dosage is maintained. Preparations for parenteral administration include sterile aqueous or non-aqueous solutions, suspensions, and emulsions. Examples of non-aqueous solvents are propylene glycol, polyethylene glycol, vegetable oils, such as olive oil, and injectable organic esters, such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives also can be present such as, for example, antimicrobials, anti-oxidants, chelating agents, and inert gases, and the like.

Compositions for oral administration include powders or granules, suspensions or solutions in water or non-aqueous media, capsules, sachets, or tablets. Thickeners, flavorings, diluents, emulsifiers, dispersing aids, or binders may be desirable.

Some of the compositions can potentially be administered as a pharmaceutically acceptable acid- or base-addition salt, foliated by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, potassium hydroxide, and organic bases, such as mono-, di-, trialkyl, and aryl amines and substituted ethanolamines.

The polypeptide (antibody), fusion protein, conjugate, nucleic acid, vector, or cell can be administered with a pharmaceutically acceptable carrier and can be delivered to the mammal's cells in vivo and/or ex vivo by a variety of mechanisms well-known in the art (e.g., uptake of naked DNA, liposome fusion, intramuscular injection of DNA via a gene gun, endocytosis, and the like).

Additionally, probiotic therapies are envisioned by the present invention. Viable host cells containing the nucleic acid or vector of the invention and expressing the polypeptide (antibody), fusion protein, or conjugate can be used directly as the delivery vehicle for the fusion protein to the desired site(s) in vivo. Preferred host cells for the delivery of the polypeptide (antibody), fusion protein, or conjugate directly to desired site(s), such as, for example, to a selected body cavity, can comprise bacteria. More specifically, such host cells can comprise suitably engineered strain(s) of lactobacilli, enterococci, or other common bacteria, such as *E. coli*, normal strains of which are known to commonly populate body cavities.

If ex vivo methods are employed, cells or tissues can be removed and maintained outside the body according to standard protocols known in the art. The compositions can be introduced into the cells via any gene transfer mechanism, such as calcium phosphate mediated gene delivery, electroporation, microinjection, or proteoliposomes. The transduced cells then can be infused (e.g., with a pharmaceutically acceptable carrier) or homotopically transplanted back into the mammal per standard methods for the cell or tissue type. Standard methods are known for transplantation or infusion of various cells into a mammal.

The exact amount of the composition required to treat a MERS-CoV infection will vary from mammal to mammal, depending on the species, age, gender, weight, and general condition of the mammal, the nature of the virus, the existence and extent of viral infection, the particular fusion proteins, nucleic acid, vector, or cell used, the route of administration, and whether other drugs are included in the regimen. Thus, it is not possible to specify an exact amount for every composition. However, an appropriate amount can be determined by one of ordinary skill in the art using only routine experimentation given the teachings herein. Effective dosages and schedules for administering the nucleic acid molecules, vectors, cells, and fusion proteins of the invention can be determined empirically, and making such determinations is within the skill in the art. The dosage ranges for the administration of the compositions are those large enough to produce the desired effect; however, the dosage should not be so large as to cause adverse side effects, such as unwanted cross-reactions, anaphylactic reactions, and the like. Dosage can vary, and can be administered in one or more (e.g., two or more, three or more, four or more, or five or more) doses daily, for one or more days. The composition can be administered before MERS-CoV infection or immediately upon determination of MERS-CoV infection and continuously administered until the virus is undetectable.

The polypeptide (antibody), fusion protein, conjugate, nucleic acid, vector, cell, or composition thereof is administered to a host (e.g., mammal, such as a human) in an amount effective to prophylactically or therapeutically inhibit a MERS-CoV infection. The efficacy of the MERS-CoV, fusion protein, conjugate, nucleic acid, vector, cell, or composition thereof as a MERS-CoV infection inhibitor may be determined by in vivo or in vitro parameters known in the art.

Any suitable dose of the polypeptide (antibody), fusion protein, conjugate, nucleic acid, vector, cell, or composition thereof can be administered to a host. The appropriate dose will vary depending upon such factors as the host's age, weight, height, sex, general medical condition, previous medical history, and MERS-CoV infection progression and can be determined by a clinician. For example, the polypeptide (antibody), fusion protein, or conjugate can be administered in a dose of about 1 µg/kg to up to 100 mg/kg of body weight or more per day (e.g., 5 µg/kg, 10 µg/kg, 50 µg/kg, 100 µg/kg, 200 µg/kg, 300 µg/kg, 400 µg/kg, 500 µg/kg, 600 µg/kg, 700 µg/kg, 800 µg/kg, 900 µg/kg, 1 mg/kg, 2 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, and ranges thereof) to the host (e.g., mammal, such as a human). Several doses (e.g., 1, 2, 3, 4, 5, 6, or more) can be provided (e.g., over a period of weeks or months).

When the vector is a viral vector, a suitable dose can include about $1 \times 10^5$ to about $1 \times 10^{12}$ (e.g., $1 \times 10^6$, $1 \times 10^7$, $1 \times 10^8$, $1 \times 10^9$, $1 \times 10^{10}$, $1 \times 10^{11}$, and ranges thereof) plaque forming units (pfus), although a lower or higher dose can be administered to a host. For example, about $2 \times 10^8$ pfus can be administered (e.g., in a volume of about 0.5 mL).

The inventive cells can be administered to a host in a dose of between about $1 \times 10^5$ and $2 \times 10^{11}$ (e.g., $1 \times 10^6$, $1 \times 10^7$, $1 \times 10^8$, $1 \times 10^9$, $1 \times 10^{10}$, and ranges thereof) cells per infusion. The cells can be administered in, for example, one to three (e.g., two) infusions. In addition to the administration of the cells, the host can be administered a biological response modifier, such as interleukin 2 (IL-2).

The polypeptide (antibody) or fusion protein can be used in combination with other well-known anti-viral therapies and/or prophylactic anti-viral vaccines already in use. The combination of the fusion protein of the invention can generate an additive or a synergistic effect with current treatments. The polypeptide (antibody) or fusion protein of the invention can be combined with other MERS-CoV therapies and vaccines, such as ribavirin and/or interferon (IFN)-α2β as described in Falzarano et al., *Nature Medicine*, 9: 1313-1317 (2013).

The following examples further illustrate the invention but, of course, should not be construed as in any way limiting its scope.

EXAMPLE 1

This example describes materials and methods for Examples 2 and 3.

Antibodies (Abs) and Other Proteins

The horseradish peroxidase (HRP)-conjugated anti-FLAG tag Ab and HRP-conjugated anti-human IgG (Fe-specific) Ab were purchased from Sigma-Aldrich (St. Louis) and anti-M13-HRP polyclonal Ab from Pharmacia (Piscataway, N.J.). The receptor binding domain (RBD) of MERS-CoV was expressed, purified, and characterized. The MERS-CoV S1 glycoprotein was purchased from Sino Biological Inc.

Large Naïve Human Antibody Library Construction

A large phage display library was constructed following published protocols for phage display (see Zhu et al., "Construction of a Large Nave Human Phage-Displayed Fab Library Through One-Step Cloning," in Therapeutic Antibodies, Volume 525, pp 129-142 (2009)) using the PBMC cDNA from 30 healthy volunteers as a template for cloning the expressed Ab gene repertoire.

Panning of the Library against Antigens

The phages ($5 \times 10^{12}$ cfu/ml) from the phage-displayed antibody library were first precipitated and then incubated with 50 nM biotinylated RBD in 1% MPBS for 30 minutes at room temperature (RT) with gentle agitation, followed by the addition of streptavidin-M280-Dynabeads for another 90 minutes of incubation. To isolate phages that bound to the antigens, the beads were washed three times with 0.05% PBST (PBS/Tween-20) with a magnetic separator (DYNAL®) to collect the beads. The phages were eluted by incubation with triethylamine (TEA) for 10 minutes followed by pH neutralization by pH 7.5 Tris-HCl. Eluted phages were used to infect E. coli TG1 cells and the phage library was prepared for the next round of panning. Three more rounds of panning were conducted as described above.

Phage ELISA

Antigens were coated on a narrow-well, 96-well plate at 50 ng/well in PBS overnight at 4° C. To determine if the phage library was enriched after panning, a polyclonal phage ELISA was performed. $10^{10}$ phage from each round of panning and the original library were incubated with immobilized antigen at 37° C. for two hours, followed by four washes with PBST. Bound phages were detected with anti-M13-HRP polyclonal Ab.

To screen the most enriched round for high affinity clones, a monoclonal phage ELISA was performed. TG1 cells were infected with phage from the fourth round of panning. Single colonies were picked from the plates and added to each well of a 96-well plate. Helper phage was then added for phage production. The phage from each well was transferred to their corresponding wells on ELISA plates coated with the antigens and incubated at 37° C. for two hours, followed by four washes with PBST. Bound phages were detected with anti-M13-HRP polyclonal Ab. The clones with the highest binding affinities were selected for further characterization.

Generation and Analysis of Soluble Fab Fragments

The selected clones were sequenced, and plasmids extracted from these clones were used for transformation of HB2151 cells. A single transformed colony was inoculated and incubated at 37 ° C. until the optical density (OD) at 600 nm reached~0.6. Isopropyl-1-thio-β-D-galactopyranoside (IPTG) was added to induce expression. After six hours of incubation at 30 ° C., the cells were lysed and the culture was centrifuged. The supernatant was used for further purification by nickel-nitrilotriacetic acid resin (Qiagen, Valencia, Calif.) according to the manufacturer's protocols. Protein purity was estimated as >95% by SDS-PAGE, and protein concentration was measured spectrophotometrically (NANOVUE™ spectrophotometer, GE Healthcare).

For the soluble Fab binding assay, the soluble Fab fragments (concentration: 10,00 to 0.45 nM at three-fold dilution) were added to a 96-well ELISA plate coated with their corresponding antigens (50 ng/well) and incubated for two hours at 37° C., followed by four washes with PBST. HRP-conjugated mouse anti-FLAG tag Ab was used to detect Fab binding. The Fabs with the highest binding affinity were selected for further characterization.

Generation and Analysis of IgG1s

The selected Fabs (Fab m336, Fab m337, Fab m338) were converted to full size antibodies in an IgG1 format. A pDR12 vector was used. The IgG1 s were expressed in the CHO mammalian cell line.

For the IgG1 binding assay, the IgG1 s (concentration: 3,333 to 4.6 nM) were added to a 96-well plate coated with their corresponding antigens (50 ng/well) and incubated for two hours at 37° C., followed by washes with PBST. HRP-conjugated goat anti-human IgG Abs were used for detection.

Neutralization Assays

Pseudovirus/cell line-based assays were used for evaluation of the neutralizing activity of the mAbs against the MERS-CoV.

Design and Engineering of Bispecific Antibody-CH3-Peptide Fusion Protein

Inhibitory peptides, genes, and primers. An inhibitory peptide (SEQ ID NO: 26) that was derived from MERS glycoprotein and can bind to membrane fusion intermediates was identified. The fusion protein genes designed for the anti-MERS fusion protein of the configuration scFv-CH3-linker-inhibitory peptide were synthesized. Conventional PCR was used to generate the negative control (CH3-linker-inhibitory peptide) using the primers set forth in Table 1.

TABLE 1

Primers used for PCR of the mAb in single chain (scFv) format, peptides, and the CH3 domain of the IqG1 Fc.

| Primer Name | Sequence |
|---|---|
| MERS-XhoI | tcgatctcgagtcaaagctctttaag (SEQ ID NO: 24) |
| MERS-neg-SfiI | catgccaccaggcccagccggccgggcagccccgagaaccac (SEQ ID NO: 25) |

Fusion protein generation. To generate the DNA encoding the fusion protein, the fusion protein genes were first inserted into the mammalian expression vector pSecTag.

After verification with gel electrophoresis, the genes generated by PCR and synthesized genes were digested with XhoI and SfiI and ligated with pSecTag vector DNA digested with the same enzymes, and used to transform ONESHOT® Top10 Chemically Competent cells (Invitrogen). Single colonies of the transformed cells were selected for sequencing. HB2151 cells were transformed with plasmids extracted from positive clones to generate DNA for transfection. Experiments to express the fusion proteins in the CHO mammalian cell line are ongoing.

EXAMPLE 2

This example demonstrates the identification and characterization of antibodies against MERS-CoV.

MERS-CoV S RBD was used for panning of a large human antibody library. Several rounds of panning under increasingly stringent conditions resulted in significant enrichment by the third and fourth rounds of panning. Individual phage clones from the fourth round of panning were screened using monoclonal phage ELISA with the same antigens used for panning. Panels of binders that exhibited the highest binding were selected for further characterization.

The phage-displayed Fabs were expressed as soluble Fabs and their binding to the corresponding antigens evaluated in an ELISA binding assay. Binding curves for the Fabs were derived by plotting optical density at 405 nm (OD405) values against Fab concentrations. The 50% binding in ELISA (EC50) was in the range from 10 nM to 100 nM. The Fabs with the lowest EC50s, three Fabs specific for the MERS-CoV RBD (Fab m336, Fab m337, Fab m338) were selected for further characterization.

These three Fabs (Fab m336, Fab m337, Fab m338) against the MERS-CoV RBD were converted to an IgG1 format. All IgG1 s against the MERS-CoV RBD bound with low subnanomolar EC50s as measured in an ELISA assay (see FIG. 2). The negative control, the IgG1 m102.4, which is specific to the Hendra and Nipah viruses, did not bind any of the antigens.

To measure the inhibitory activity of the antibodies, assays based on pseudoviruses were used. The RBD-specific mAbs exhibited exceptionally potent neutralizing activity, inhibiting >95% of viral entry at the lowest concentration tested (0.1 µg/ml) (see FIG. 1). Although the pseudovirus only displayed spike glycoprotein (S) on the viral envelope, this result demonstrates that the anti-MERS-CoV mAbs can successfully and specifically bind to spike glycoprotein (S) as surface glycoproteins and prevent viral fusion.

In summary, the anti-MERS-CoV mAbs in their IgG1 format bound to its RBD with very high avidity (subnanomolar) and neutralized the virus in vitro in a pseudovirus assay with exceptional potency. Although not wishing to be bound by any particular theory, a likely mechanism of the anti-MERS-CoV mAbs neutralizing activity is competition with the receptor (CD26) for binding to spike glycoprotein (S) (see Lu et al., Nature, 500: 227-231 (2013)). It appears that the mAbs to MERS-CoV bind to epitopes which overlap the receptor binding site of spike glycoprotein (S).

The anti-MERS-CoV mAbs will be tested using mouse and monkey models infected with live MERS-CoV to confirm that the anti-MERS-CoV mAbs effectively prevent and treat infection in vivo.

EXAMPLE 3

This example demonstrates the production of bispecific antibodies against MERS-CoV.

Bispecific antibody-based molecules were designed to increase the potency and breadth of neutralization and decrease the probability for development of resistance. The bispecific molecules are fusion proteins of a mAb against the spike glycoprotein (S) (e.g., an scFv) linked to an inhibitory peptide that binds to membrane fusion intermediates.

Virus entry into cells occurs in two major pathways: the endocytic and no-endocytic routes. The endocytic route includes clathrin-mediated endocytosis and penetration (e.g., adenoviruses, influenza, and other viruses fuse within the cell after endocytosis). The non-endocytic route includes fusion at the cell surface (e.g., HIV, coronaviruses, and other viruses fuse mostly at the cell surface).

For MERS-CoV, virus entry into cells is mediated by spike glycoprotein (S). The RBD on S mediates the attachment of the virus to its cellular receptor (CD26).

The antibody binds to the virus and can inhibit entry to certain extent; however, in the presence of inhibitory peptides, the viruses that were not inhibited could be further neutralized by the peptides, which bind to fusion intermediates and inhibit membrane fusion.

MERS-CoV can fuse both at the cell surface and inside an endosome. Therefore, it is preferable that the antibody be joined with the inhibitory peptide by a non-cleavable linker. This is because if the peptide is cleaved at the cell surface, the peptide could quickly diffuse in the bulk of the environment, resulting in a dramatic decrease in local concentration and reduced inhibitory activity.

Based on these considerations and estimations, a fusion protein with a long, flexible non-cleavable linker joining the inhibitory peptide to the engineered antibody against MERS-CoV was designed (see FIG. 3). The DNA construct was successfully generated and protein expression and characterization is ongoing. The fusion protein has the configuration of scFv-CH3-linker-inhibitory peptide (e.g., SEQ ID NO: 23).

The mAbs against the MERS-CoV and the engineered antibody-fusion protein against MERS-CoV will be also characterized in animal models for their safety, efficacy, and pharmacokinetics, in preparation for their use as therapeutics against MERS-CoV.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A polypeptide comprising:

(a) an immunoglobulin heavy chain variable region (VH) comprising SEQ ID NO: 3 (HCDR1), SEQ ID NO: 4 (HCDR2), and SEQ ID NO: 5 (HCDR3), and an immunoglobulin light chain variable region (VL) comprising SEQ ID NO: 6 (LCDR1), SEQ ID NO: 7 (LCDR2), and SEQ ID NO: 8 (LCDR3);

(b) an immunoglobulin heavy chain variable region (VH) comprising SEQ ID NO: 11 (HCDR1), SEQ ID NO: 4 (HCDR2), SEQ ID NO: 12 (HCDR3), and an immunoglobulin light chain variable region (VL) comprising SEQ ID NO: 13 (LCDR1), SEQ ID NO: 14 (LCDR2), and SEQ ID NO: 15 (LCDR3); or (c) an immunoglobulin heavy chain variable region (VH) comprising SEQ ID NO: 11 (HCDR1), SEQ ID NO: 18 (HCDR2), SEQ ID NO: 19 (HCDR3), and an immunoglobulin light chain variable region (VL) comprising SEQ ID NO: 20 (LCDR1), SEQ ID NO: 21 (LCDR2), and SEQ ID NO: 22 (LCDR3).

2. The polypeptide of claim 1 comprising an immunoglobulin heavy chain variable region (VH region) comprising SEQ ID NO: 3 (HCDR1), SEQ ID NO: 4 (HCDR2), SEQ ID NO: 5 (HCDR3), and an immunoglobulin light chain variable region (VL region) comprising SEQ ID NO: 6 (LCDR1), SEQ ID NO: 7 (LCDR2), and SEQ ID NO: 8 (LCDR3).

3. The polypeptide of claim 2, wherein the VH region comprises SEQ ID NO: 1 and the VL region comprises SEQ ID NO: 2.

4. The polypeptide of claim 1, wherein the polypeptide is a monoclonal antibody or fragment thereof.

5. The polypeptide of claim 1, wherein the polypeptide is an Fab, Fab', F(ab')2, scFv, di-scFv, or fusion protein, or conjugate thereof.

6. The polypeptide of claim 1, wherein the polypeptide further comprises a MERS-CoV inhibitory peptide.

7. The polypeptide of claim 1, wherein the polypeptide further comprises a CH3 antibody dimerization domain sequence.

8. The polypeptide of claim 1, wherein the polypeptide comprises the amino acid sequence of SEQ ID NO: 23.

9. The polypeptide of claim 1, wherein the polypeptide binds with an epitope of the receptor binding domain (RBD) of spike (S) glycoprotein of the Middle East Respiratory Syndrome Coronavirus (MERS-CoV).

10. A pharmaceutical composition comprising the polypeptide of claim 1 and a pharmaceutically acceptable carrier.

11. The composition of claim 10, wherein the composition further comprises an additional active agent.

12. The composition of claim 11, wherein the additional active agent is selected from the group consisting of interleukin (IL)-2, IL-12, IL 7, and combinations thereof.

13. The polypeptide of claim 6, wherein the MERS-CoV inhibitory peptide comprises SEQ ID NO: 26.

14. The polypeptide of claim 6, further comprising a CH3 antibody dimerization domain sequence.

15. A dimer of two polypeptides of claim 14.

16. The composition of claim 11, wherein the additional active agent is selected from the group consisting of Cyclosporin A.

17. The composition of claim 11, wherein the additional active agent is an inactivated virus.

18. The composition of claim 11, wherein the additional active agent comprises CD40 ligand and IL-12.

19. The composition of claim 11, wherein the additional active agent is ribavirin.

20. The composition of claim 11, wherein the additional active agent is an interferon.

* * * * *

SEQUENCE LISTING

```
<160> NUMBER OF SEQ ID NOS: 28

<210> SEQ ID NO 1
<211> LENGTH: 455
<212> TYPE: PRT
<213> ORGANISM: Artificial Sequence
<220> FEATURE:
<223> OTHER INFORMATION: Synthetic

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Ser Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gly Tyr Cys Ser Ser Thr Ser Cys Asn Arg Gly Ala Phe
            100                 105                 110

Asp Ile Trp Gly Gln Gly Thr Met Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160
```

```
Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 2
<211> LENGTH: 214
<212> TYPE: PRT
<213> ORGANISM: Artificial Sequence
<220> FEATURE:
<223> OTHER INFORMATION: Synthetic

<400> SEQUENCE: 2

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Leu
             85                  90                  95

Thr Phe Gly Gly Gly Thr Lys Val Glu Ile Lys Arg Thr Val Ala Ala
         100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 8
<212> TYPE: PRT
<213> ORGANISM: Artificial Sequence
<220> FEATURE:
<223> OTHER INFORMATION: Synthetic

<400> SEQUENCE: 3

Gly Gly Thr Phe Ser Ser Tyr Ala
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Ile Ile Pro Ile Phe Gly Thr Ala
1               5

<210> SEQ ID NO 5
<211> LENGTH: 18
<212> TYPE: PRT
<213> ORGANISM: Artificial Sequence
<220> FEATURE:
<223> OTHER INFORMATION: Synthetic

<400> SEQUENCE: 5

Ala Arg Val Gly Tyr Cys Ser Ser Thr Ser Cys Asn Arg Gly Ala Phe
1               5                   10                  15

Asp Ile

<210> SEQ ID NO 6
<211> LENGTH: 6
<212> TYPE: PRT
<213> ORGANISM: Artificial Sequence
<220> FEATURE:
<223> OTHER INFORMATION: Synthetic -continued

<400> SEQUENCE: 6

Gln Gly Ile Arg Asn Asp
1               5

<210> SEQ ID NO 7
<211> LENGTH: 3
<212> TYPE: PRT
<213> ORGANISM: Artificial Sequence
<220> FEATURE:
<223> OTHER INFORMATION: Synthetic

<400> SEQUENCE: 7

Ala Ala Ser
1

<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8

Gln Gln Leu Asn Ser Tyr Pro
1               5

<210> SEQ ID NO 9
<211> LENGTH: 459
<212> TYPE: PRT
<213> ORGANISM: Artificial Sequence
<220> FEATURE:
<223> OTHER INFORMATION: Synthetic

<400> SEQUENCE: 9

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Leu Gly Pro Gly Gly Asp Ser Ser Gly Tyr Tyr Tyr Gly
            100                 105                 110

Pro Gly Ala Phe Asp Ile Trp Gly Gln Gly Thr Met Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln

```
              195                 200                 205
Thr Tyr Ile Cys Asn Val Asn His Lys Pro Ser Asn Thr Lys Val Asp
    210                 215                 220
Lys Lys Val Glu Pro Lys Ser Cys Asp Lys Thr His Thr Cys Pro Pro
225                 230                 235                 240
Cys Pro Ala Pro Glu Leu Leu Gly Gly Pro Ser Val Phe Leu Phe Pro
                245                 250                 255
Pro Lys Pro Lys Asp Thr Leu Met Ile Ser Arg Thr Pro Glu Val Thr
            260                 265                 270
Cys Val Val Val Asp Val Ser His Glu Asp Pro Glu Val Lys Phe Asn
        275                 280                 285
Trp Tyr Val Asp Gly Val Glu Val His Asn Ala Lys Thr Lys Pro Arg
    290                 295                 300
Glu Glu Gln Tyr Asn Ser Thr Tyr Arg Val Val Ser Val Leu Thr Val
305                 310                 315                 320
Leu His Gln Asp Trp Leu Asn Gly Lys Glu Tyr Lys Cys Lys Val Ser
                325                 330                 335
Asn Lys Ala Leu Pro Ala Pro Ile Glu Lys Thr Ile Ser Lys Ala Lys
            340                 345                 350
Gly Gln Pro Arg Glu Pro Gln Val Tyr Thr Leu Pro Pro Ser Arg Asp
        355                 360                 365
Glu Leu Thr Lys Asn Gln Val Ser Leu Thr Cys Leu Val Lys Gly Phe
    370                 375                 380
Tyr Pro Ser Asp Ile Ala Val Glu Trp Glu Ser Asn Gly Gln Pro Glu
385                 390                 395                 400
Asn Asn Tyr Lys Thr Thr Pro Pro Val Leu Asp Ser Asp Gly Ser Phe
                405                 410                 415
Phe Leu Tyr Ser Lys Leu Thr Val Asp Lys Ser Arg Trp Gln Gln Gly
            420                 425                 430
Asn Val Phe Ser Cys Ser Val Met His Glu Ala Leu His Asn His Tyr
        435                 440                 445
Thr Gln Lys Ser Leu Ser Leu Ser Pro Gly Lys
    450                 455

<210> SEQ ID NO 10
<211> LENGTH: 219
<212> TYPE: PRT
<213> ORGANISM: Artificial Sequence
<220> FEATURE:
<223> OTHER INFORMATION: Synthetic

<400> SEQUENCE: 10

Glu Ile Val Leu Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Ser
            20                  25                  30
Asn Gly Tyr Asn Tyr Leu Asp Trp Tyr Leu Gln Lys Pro Gly Lys Ser
        35                  40                  45
Pro Gln Leu Leu Ile Tyr Leu Gly Ser Asn Arg Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Leu Gln Thr Pro Leu Thr Phe Gly Gly Gly Thr Lys Val Glu Ile Lys
```

```
                100                 105                 110
Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 11
<211> LENGTH: 8
<212> TYPE: PRT
<213> ORGANISM: Artificial Sequence
<220> FEATURE:
<223> OTHER INFORMATION: Synthetic

<400> SEQUENCE: 11

```
Gly Gly Thr Phe Ser Ser Tyr Thr
1               5
```

<210> SEQ ID NO 12
<211> LENGTH: 22
<212> TYPE: PRT
<213> ORGANISM: Artificial Sequence
<220> FEATURE:
<223> OTHER INFORMATION: Synthetic

<400> SEQUENCE: 12

```
Ala Arg Asp Leu Gly Pro Gly Gly Asp Ser Ser Gly Tyr Tyr Tyr Gly
1               5                   10                  15

Pro Gly Ala Phe Asp Ile
            20
```

<210> SEQ ID NO 13
<211> LENGTH: 11
<212> TYPE: PRT
<213> ORGANISM: Artificial Sequence
<220> FEATURE:
<223> OTHER INFORMATION: Synthetic

<400> SEQUENCE: 13

```
Gln Ser Leu Leu His Ser Asn Gly Tyr Asn Tyr
1               5                   10
```

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

```
Leu Gly Ser
1
```

<210> SEQ ID NO 15
<211> LENGTH: 7
<212> TYPE: PRT
<213> ORGANISM: Artificial Sequence
<220> FEATURE:
<223> OTHER INFORMATION: Synthetic

<400> SEQUENCE: 15

Met Gln Ala Leu Gln Thr Pro
1               5

<210> SEQ ID NO 16
<211> LENGTH: 456
<212> TYPE: PRT
<213> ORGANISM: Artificial Sequence
<220> FEATURE:
<223> OTHER INFORMATION: Synthetic

<400> SEQUENCE: 16

Gln Val Gln Leu Gln Gln Ser Gly Ala Glu Val Lys Lys Arg Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Leu Tyr Asp Ser Ser Gly Tyr Tyr Arg Asn Thr Asp Ala
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

```
Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
            325                 330                 335

Leu Pro Ala Pro Ile Glu Lys Thr Ile Ser Lys Ala Lys Gly Gln Pro
        340                 345                 350

Arg Glu Pro Gln Val Tyr Thr Leu Pro Pro Ser Arg Asp Glu Leu Thr
    355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 17
<211> LENGTH: 214
<212> TYPE: PRT
<213> ORGANISM: Artificial Sequence
<220> FEATURE:
<223> OTHER INFORMATION: Synthetic

<400> SEQUENCE: 17

Glu Ile Val Met Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Gly Ser Ser Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210

<210> SEQ ID NO 18
<211> LENGTH: 8
<212> TYPE: PRT
<213> ORGANISM: Artificial Sequence
<220> FEATURE:
<223> OTHER INFORMATION: Synthetic

<400> SEQUENCE: 18

Ile Ile Pro Ile Leu Gly Ile Ala
1               5

<210> SEQ ID NO 19
<211> LENGTH: 19
<212> TYPE: PRT
<213> ORGANISM: Artificial Sequence
<220> FEATURE:
<223> OTHER INFORMATION: Synthetic

<400> SEQUENCE: 19

Ala Arg Asp Leu Tyr Asp Ser Ser Gly Tyr Tyr Arg Asn Thr Asp Ala
1               5                   10                  15

Phe Asp Ile

<210> SEQ ID NO 20
<211> LENGTH: 6
<212> TYPE: PRT
<213> ORGANISM: Artificial Sequence
<220> FEATURE:
<223> OTHER INFORMATION: Synthetic

<400> SEQUENCE: 20

Gln Ser Val Ser Ser Tyr
1               5

<210> SEQ ID NO 21
<211> LENGTH: 3
<212> TYPE: PRT
<213> ORGANISM: Artificial Sequence
<220> FEATURE:
<223> OTHER INFORMATION: Synthetic

<400> SEQUENCE: 21

Asp Ala Ser
1

<210> SEQ ID NO 22
<211> LENGTH: 7
<212> TYPE: PRT
<213> ORGANISM: Artificial Sequence
<220> FEATURE:
<223> OTHER INFORMATION: Synthetic

<400> SEQUENCE: 22

Gln Gln Tyr Gly Ser Ser Pro
1               5

<210> SEQ ID NO 23
<211> LENGTH: 432
<212> TYPE: PRT
<213> ORGANISM: Artificial Sequence
<220> FEATURE:
<223> OTHER INFORMATION: Synthetic

<400> SEQUENCE: 23
```

```
Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
             20                  25                  30

Leu Gly Trp Tyr Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65              70                  75                  80

Glu Asp Phe Ala Thr Tyr Tyr Cys Gln Gln Leu Asn Ser Tyr Pro Leu
                 85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Gln Val Gln Leu Val Gln
        115                 120                 125

Ser Gly Ala Glu Val Lys Lys Pro Gly Ser Ser Val Lys Val Ser Cys
 130                 135                 140

Lys Ala Ser Gly Gly Thr Phe Ser Ser Tyr Ala Ile Ser Trp Val Arg
145                 150                 155                 160

Gln Ala Pro Gly Gln Gly Leu Glu Trp Met Gly Gly Ile Ile Pro Ile
                 165                 170                 175

Phe Gly Thr Ala Ser Tyr Ala Gln Lys Phe Gln Gly Arg Val Thr Ile
             180                 185                 190

Thr Ala Asp Lys Ser Thr Ser Thr Ala Tyr Met Glu Leu Ser Ser Leu
             195                 200                 205

Arg Ser Glu Asp Thr Ala Val Tyr Tyr Cys Ala Arg Val Gly Tyr Cys
210                 215                 220

Ser Ser Thr Ser Cys Asn Arg Gly Ala Phe Asp Ile Trp Gly Gln Gly
225                 230                 235                 240

Thr Met Val Thr Val Ser Ser Asp Lys Thr His Thr Cys Pro Pro Cys
             245                 250                 255

Pro Gly Gly Gly Ser Gly Gln Pro Arg Glu Pro Gln Val Tyr Thr
             260                 265                 270

Leu Pro Pro Ser Arg Asp Glu Leu Thr Lys Asn Gln Val Ser Leu Thr
             275                 280                 285

Cys Leu Val Lys Gly Phe Tyr Pro Ser Asp Ile Ala Val Glu Trp Glu
 290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
             325                 330                 335

Ser Arg Trp Gln Gln Gly Asn Val Phe Ser Cys Ser Val Met His Glu
             340                 345                 350

Ala Leu His Asn His Tyr Thr Gln Lys Ser Leu Ser Leu Ser Pro Gly
         355                 360                 365

Lys Gly Gly Gly Gly Ser His His His His His His Gly Gly
     370                 375                 380

Gly Gly Ser Gly Gly Gly Ser Gly Gly Gly Ser Leu Thr Gln
385                 390                 395                 400

Ile Asn Thr Thr Leu Leu Asp Leu Thr Tyr Glu Met Leu Ser Leu Gln
             405                 410                 415
```

Gln Val Val Lys Ala Leu Asn Glu Ser Tyr Ile Asp Leu Lys Glu Leu
           420                 425                 430

<210> SEQ ID NO 24
<211> LENGTH: 26
<212> TYPE: DNA
<213> ORGANISM: Artificial Sequence
<220> FEATURE:
<223> OTHER INFORMATION: Synthetic

<400> SEQUENCE: 24
tcgatctcga gtcaaagctc tttaag                                         26

<210> SEQ ID NO 25
<211> LENGTH: 42
<212> TYPE: DNA
<213> ORGANISM: Artificial Sequence
<220> FEATURE:
<223> OTHER INFORMATION: Synthetic

<400> SEQUENCE: 25
catgccacca ggcccagccg gccgggcagc ccgagaaacc ac                        42

<210> SEQ ID NO 26
<211> LENGTH: 35
<212> TYPE: PRT
<213> ORGANISM: Artificial Sequence
<220> FEATURE:
<223> OTHER INFORMATION: Synthetic

<400> SEQUENCE: 26

Leu Thr Gln Ile Asn Thr Thr Leu Leu Asp Leu Thr Tyr Glu Met Leu
1               5                   10                  15

Ser Leu Gln Gln Val Val Lys Ala Leu Asn Glu Ser Tyr Ile Asp Leu
            20                  25                  30

Lys Glu Leu
        35

<210> SEQ ID NO 27
<211> LENGTH: 107
<212> TYPE: PRT
<213> ORGANISM: Artificial Sequence
<220> FEATURE:
<223> OTHER INFORMATION: Synthetic

<400> SEQUENCE: 27

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 28

-continued

```
<211> LENGTH: 15
<212> TYPE: PRT
<213> ORGANISM: Artificial Sequence
<220> FEATURE:
<223> OTHER INFORMATION: Synthetic

<400> SEQUENCE: 28

Gly Gly Gly Gly Ser Gly Gly Gly Gly Ser Gly Gly Gly Gly Ser
1               5                   10                  15
```

UNITED STATES PATENT AND TRADEMARK OFFICE
CERTIFICATE OF CORRECTION

PATENT NO. : 10,421,802 B2
APPLICATION NO. : 15/030165
DATED : September 24, 2019
INVENTOR(S) : Dimiter S. Dimitrov et al.

It is certified that error appears in the above-identified patent and that said Letters Patent is hereby corrected as shown below:

On the Title Page

Under abstract "20 Claims, 3 Drawing Sheets" should read -21 Claims, 3 Drawing Sheets-.

In the Claims

Column 40 Line 47 The following claim is added after Claim 20:
21. A method of inhibiting a MERS-COV infection in a mammal, which method comprises administering to the mammal:
    (a) the polypeptide of claim 1; or
    (b) a pharmaceutical composition comprising the polypeptide of claim 1 and a pharmaceutically acceptable carrier;
    wherein the MERS-COV infection is inhibited.

Signed and Sealed this
Twenty-fourth Day of March, 2020

Andrei Iancu
*Director of the United States Patent and Trademark Office*